(12) United States Patent
Davis

(10) Patent No.: US 8,672,128 B2
(45) Date of Patent: Mar. 18, 2014

(54) CONTAINER FOR SANITIZING AN ARTICLE

(75) Inventor: Colin Davis, Kaneohe, HI (US)

(73) Assignee: Dr. Tung's Products, Kaneohe, HI (US)

( * ) Notice: Subject to any disclaimer, the term of this patent is extended or adjusted under 35 U.S.C. 154(b) by 1097 days.

(21) Appl. No.: 11/591,838

(22) Filed: Nov. 2, 2006

(65) Prior Publication Data

US 2007/0181448 A1 Aug. 9, 2007

Related U.S. Application Data

(63) Continuation-in-part of application No. 11/350,504, filed on Feb. 9, 2006, now abandoned.

(51) Int. Cl.
*B65D 83/10* (2006.01)

(52) U.S. Cl.
USPC .......... 206/362.3; 206/362.2; 206/209.1; 206/209; 206/361; 206/205

(58) Field of Classification Search
USPC ........ 206/362.3, 362.2, 209.1, 209, 361, 205, 206/207, 213.1
See application file for complete search history.

(56) References Cited

U.S. PATENT DOCUMENTS

| | | |
|---|---|---|
| 1,041,315 A | 10/1912 | Marx |
| 1,194,540 A | 8/1916 | Quartararo |
| 1,470,129 A | 10/1923 | Tichenor |
| 2,043,629 A | 6/1936 | Lyon |
| 2,576,550 A | 11/1951 | Waters |
| 3,127,985 A | 4/1964 | Scott |
| 3,746,162 A | 7/1973 | Bridges |
| 3,884,635 A | 5/1975 | Sloan |
| 4,214,657 A | 7/1980 | Winston |
| 4,728,504 A | 3/1988 | Nichols |
| 4,735,358 A * | 4/1988 | Morita et al. ...................... 239/1 |
| 5,788,061 A * | 8/1998 | Hammond .................... 206/0.5 |
| 5,960,801 A * | 10/1999 | Vermooten et al. ........... 132/308 |
| 5,961,958 A * | 10/1999 | Homola et al. ................. 424/49 |
| 6,099,861 A * | 8/2000 | DeSenna et al. ............. 424/466 |
| 2002/0058604 A1* | 5/2002 | Kischkel et al. ............. 510/446 |

FOREIGN PATENT DOCUMENTS

GB 1 210 813 11/1970

* cited by examiner

*Primary Examiner* — Anthony Stashick
*Assistant Examiner* — Blaine Neway
(74) *Attorney, Agent, or Firm* — Pauley Petersen & Erickson

(57) ABSTRACT

A container for sanitizing an article includes a case defining a central void sized to accommodate at least a portion of the article, a receptacle in fluid communication with the central void, and a granular, antiseptic media disposed within the receptacle. The granular, antiseptic media includes at least one out-gassing, antimicrobial agent such as, thyme oil or thymol. The granular, antiseptic media may further include a granular, fragrance blended with the granular, out-gassing, antimicrobial agent in a select ratio to remediate an antiseptic odor of the out-gassing, antimicrobial agent. The article may be a toothbrush or other type of brush, a mouth guard, a comb, a sponge, or other article which may be stored in a damp or wet condition after use.

19 Claims, 6 Drawing Sheets

CONTAINER FOR SANITIZING AN ARTICLE

RELATED APPLICATIONS

This application is a continuation-in-part of U.S. patent application Ser. No. 11/350,504 filed on 9 Feb. 2006 now abandoned. The disclosure of the prior application is incorporated herein by reference.

BACKGROUND OF THE INVENTION

1. Field of the Invention

The present invention provides improvements to containers and antiseptics for sanitizing an article such as, for example, a brush, a toothbrush, a comb or similar articles.

2. Discussion of the Related Art

Several kinds of toothbrush holders or covers are known in the art, including those with tableted, antiseptic out-gassing media such as one described in U.S. Pat. No. 5,960,801, to Vermooten et al.

A number of out-gassing sanitizing or antimicrobial agents which may be used in the antiseptic media generally have a strong herbaceous, antiseptic and/or medicinal vapor which may be unappealing and/or offensive when used for germ-killing applications in the home. Such herbaceous, medicinal or antiseptic aroma typically does not create a soothing environment and may be disadvantageous when the out-gassing antiseptic media is used, for example, as a toothbrush sanitizer.

Conventional methods for reducing or remediating a strong odor or aroma of a sanitizing or antimicrobial agent typically involve blending the agent in a liquid form with other fragrant oils or liquids such as, for example, is done in aromatherapy or perfume production, to produce a blended composition having a generally more pleasing or acceptable aroma. Some out-gassing, antimicrobial agents such as, for example, thyme oil, thymol, eucalyptol, tea tree oil, oregano oil, cedrol, terpineol and anethol, have such a strong odor or aroma that unless the relative percentage of the out-gassing, antimicrobial agent in the blended composition is significantly decreased the strong odor prevails. However, reducing the amount of out-gassing, antimicrobial agent in the blend is generally disadvantageous due to reduced potency or antimicrobial efficacy of the blend as a whole and the increased costs associated with using a larger quantity of the blend to achieve comparable results.

In view of the problems or challenges described above, improvements are desired over the structures and antiseptic media of the known art in order to achieve improved safety, functionality and ease of manufacture for containers of the antiseptic type.

SUMMARY OF THE INVENTION

The objective of the invention can be achieved, at least in part, through a container for sanitizing an article which includes a case defining a central void and a receptacle in fluid communication with the central void. The case is sized to accommodate at least a portion of the article which may be a brush, a toothbrush, a comb or the like. The container further includes a granular, antiseptic media disposed within the receptacle. The granular, antiseptic media includes an out-gassing, antimicrobial agent selected from, for example, thyme oil, thymol, oregano oil, carvacrol, tea tree oil, terpineol, eucalyptol, clove oil, cinnamon oil, eugenol, cinnamic acid, peppermint oil, menthol, geraniol, verbenone, cedrol, pinocarvone, anethol, hinokitiol, berberine, ferulic acid, methyl salicylic acid, methyl salicylate, limonene, or a derivative thereof.

In accordance with another embodiment, a container for sanitizing an article includes a case defining a central void, the central void sized to accommodate at least a portion of the article, and a receptacle in fluid communication with the central void. A granular, antiseptic media is disposed within the receptacle. The granular, antiseptic media includes a first inert particulate carrier impregnated with an out-gassing, antimicrobial agent and a second inert particulate carrier impregnated with a fragrance. The fragrance may be an essential oil such as, for example, cinnamon oil, a scented oil, or a combination thereof. The first and/or second inert particulate carrier material may be a natural particulate material such as, for example, corn cobs or clays, or porous beads such as, for example, aroma beads.

In a further embodiment, a container for sanitizing an article includes a case defining a central void, the central void sized to accommodate at least a portion of the article, and a receptacle in fluid communication with the central void. The receptacle contains a granular, antiseptic media including a first granular corn cob media impregnated with thyme oil and a second granular corn cob media impregnated with a fragrance such as, for example, cinnamon oil.

The present invention further comprehends a method for making the granular, antiseptic media used in the container. The method includes impregnating a first inert particulate carrier with an out-gassing, antimicrobial agent to produce disinfectant granules, impregnating a second inert particulate carrier with a fragrance to produce fragrance granules, and blending the disinfectant granules with the fragrance granules in a select ratio to remediate an antiseptic odor of the disinfectant granules.

Words of degree, such as "about", "substantially", and the like are used herein in the sense of "at, or nearly at, when given the manufacturing, design, and material tolerances inherent in the stated circumstances" and are used to prevent the unscrupulous infringer from unfairly taking advantage of the invention disclosure where exact or absolute figures are stated as an aid to understanding the invention.

BRIEF DESCRIPTION OF THE DRAWINGS

The aspects of this invention will be better understood from the following detailed description taken in conjunction with the drawings wherein.

DETAILED DESCRIPTION OF THE INVENTION

Figure 1:
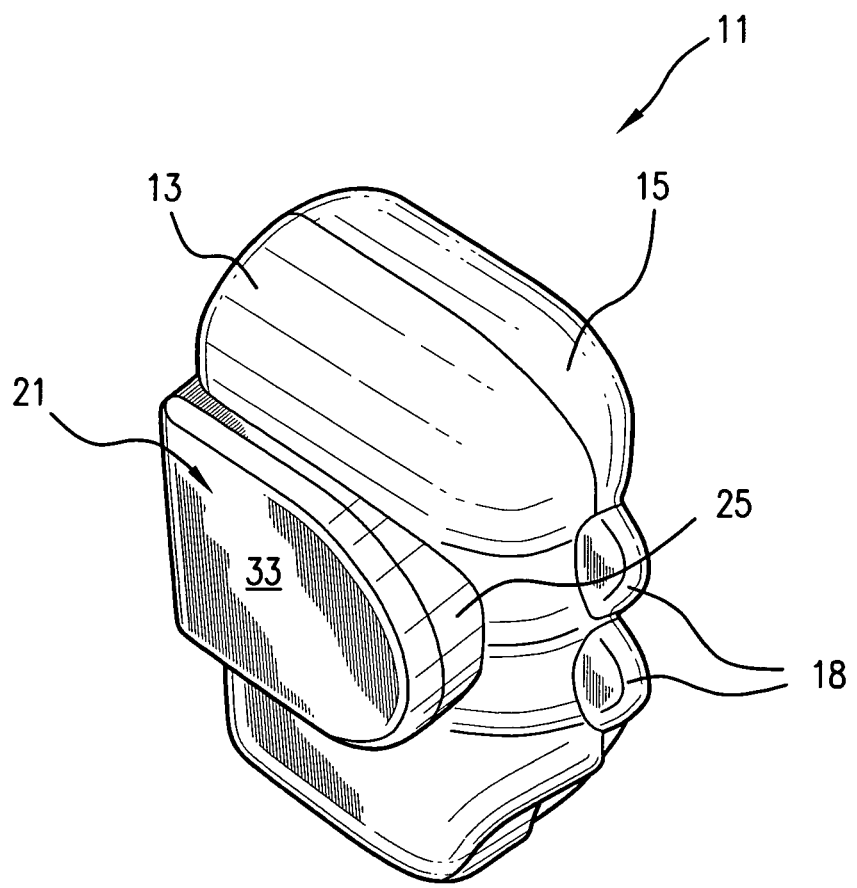
FIG. 1 is an exterior front perspective view of a closed toothbrush cover with the receptacle covering in place and an opaque receptacle wall.

The present invention is directed to a container for sanitizing an article, a granular, antiseptic media for use in the container, and a method for preparing the granular, antiseptic media. The container includes a case which defines a central void or cavity sized to accommodate at least a portion of the article. For example, the case may be sized to accommodate the whole of the article within the central void. In accordance with certain other embodiments, the case may be sized to accommodate a portion of the article such as, for example, a head, tip or end portion of the article within the central void. In such embodiments, the case may further include an opening or cutout to accommodate the portion of the article which is not contained within the central void.

Generally, the article may include any item or implement which is typically stored, after use, in a wet or damp condition or environment wherein proliferation of undesirable contaminants such as bacteria, mold or viral organisms is encouraged or supported. The article may be, for example, a personal care article including, but not limited to, toothbrushes, hairbrushes, combs, make-up brushes, mouth guards, dentures, tooth whitening trays, razors, or the like; a cleaning implement including, but not limited to, scrub brushes, toilet brushes, sponges, bottle brushes or the like; or a food preparation implement such as, for example, vegetable brushes, pastry brushes, basting brushes or the like.

The container further includes a receptacle or holder which is in fluid communication with the central void. In accordance with certain embodiments, the receptacle or holder is integrally formed in a wall of the case. In accordance with certain other embodiments, the receptacle or holder is contained within the central void. For example, the case may include an interior wall which divides the central void into a receptacle or holder for containing a granular antiseptic media and a cavity for containing at least a portion of the article. Alternatively, the receptacle or holder may be formed on an interior surface of a wall of the case such that the receptacle or holder extends into and/or is contained within the central void.

Advantageously, the receptacle is sized to accommodate a select, efficacious, and/or desired amount of a granular, antiseptic media which is effective to prevent or inhibit the proliferation of undesirable microbial species such as, for example, bacteria, mold and/or viral organisms. Suitably, the receptacle and/or the case includes a gas permeable covering which forms a barrier between the receptacle and the central void to retain or contain the granular, antiseptic media within the receptacle. In accordance with certain embodiment, the covering or barrier may be a perforated material such as, for example, a perforated plastic or polymer cover, mesh, netting, gas permeable membrane or any other material which readily allows sanitizing or antiseptic vapors produced by the granular, antiseptic media to pass from the receptacle into the central void of the case while retaining the granular, antiseptic media within the receptacle.

Figure 2:
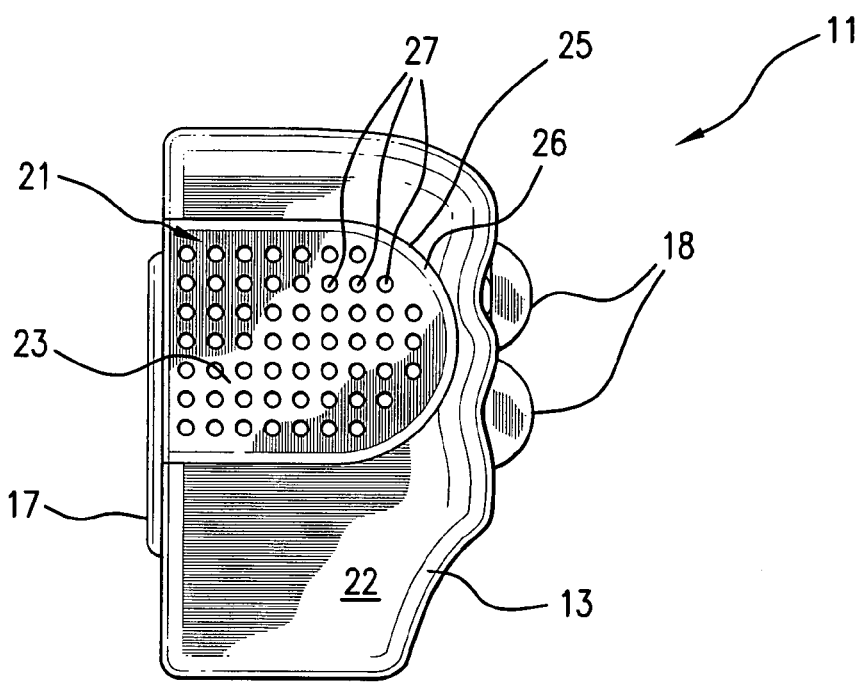
FIG. 2 is an exterior side view of a first portion of the toothbrush cover with the receptacle covering removed and the case in the closed position.
Figure 3:
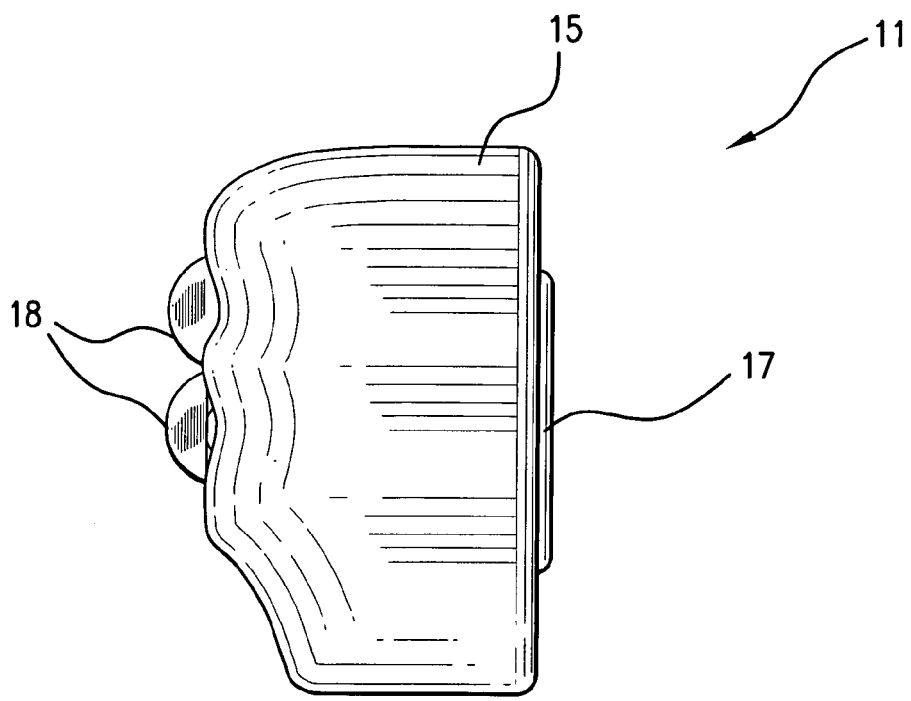
FIG. 3 is an exterior side view of a second portion of the toothbrush cover with the case in the closed position.
Figure 4:
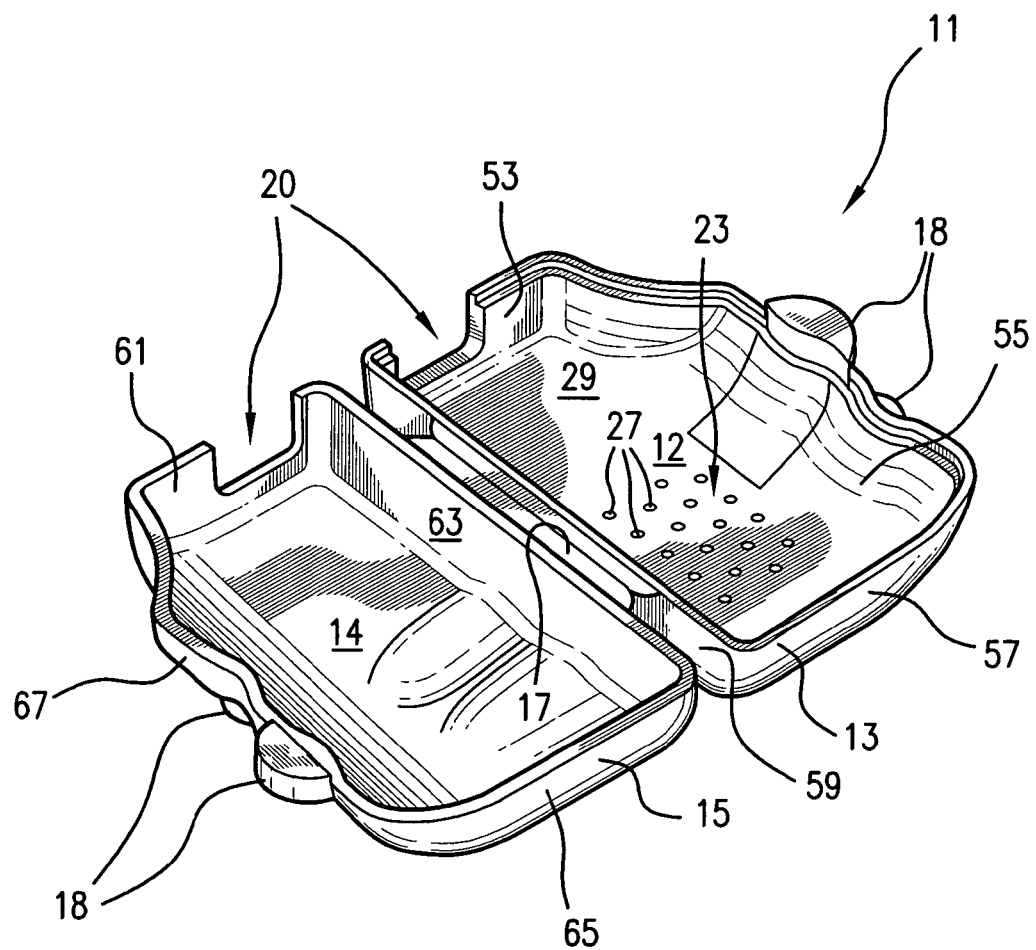
FIG. 4 is an interior perspective view of the tooth brush cover in the open position.

Referring to the drawing FIGS. 1-5, an exemplary container for sanitizing an article in the form of an antiseptic toothbrush cover is illustrated. According to one embodiment of the invention, the antiseptic toothbrush cover comprises a one-piece molded case 11, sometimes referred to as a "clamshell" case, such as may be molded or pressed from plastic, laminated paperboard, or other suitable material. The case 11 is divided between generally bowl-shaped portions being a first portion 13 and a second portion 15. Referring especially to FIG. 4, while shown as contoured, the first and second case portions 13, 15 may alternatively be generally be described as each being a substantially open-faced parallelepiped with five walls, and with a major surface, i.e., wall of greatest area, referred to as a lid 12, 14, and four side walls, 53, 55, 57, 59 and 61, 63, 65, 67; respectively, with the open faces being opposite the lids 12, 14. In either event, the case portions desirably have a majority of smooth, rounded, and uninterrupted interior surfaces to minimize nooks and crannies where bacteria may hide. It will occur to the person of skill in the art that other general case configurations for creating a central void for containing a toothbrush, or the head thereof, may be utilized within the scope of the current invention.

Figure 5:
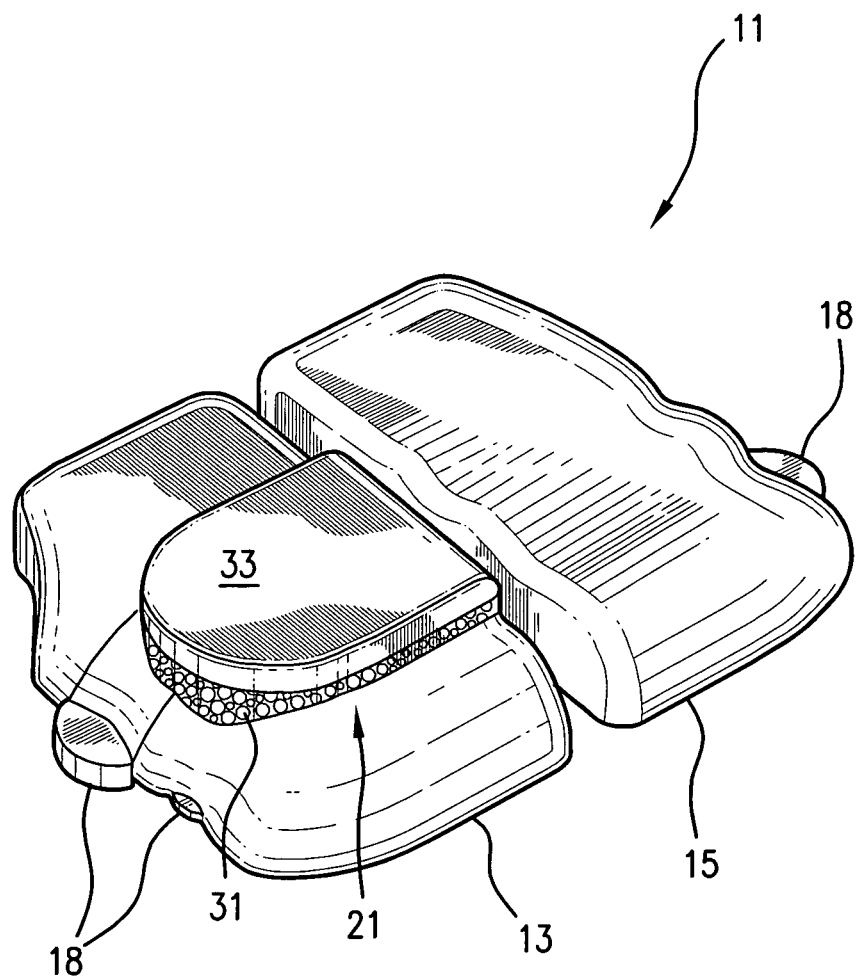
FIG. 5 is an exterior perspective view of the tooth brush cover in the open position with the receptacle covering in place and a translucent receptacle wall showing the antiseptic media within the receptacle.

A hinge, desirably such as living hinge 17, (FIGS. 2-4) connects the first portion 13 and the second portion 15 and allows the case 11 an open position, as in FIG. 4 and FIG. 5, for easy removal and insertion of a toothbrush (not shown) and a closed position, as in FIGS. 1-3, whereby the first portion 13 and the second portion 15 are positioned to form a substantially enclosed void for holding at least a head of the toothbrush (not shown), i.e. the part with bristles. A clasp mechanism 18 is desirably integrally formed in the case 11 for holding the case 11 in the closed position. Opposing cutouts, collectively 20, (FIG. 4) are formed on corresponding surfaces of the first portion 13 and the second portion 15 to permit exit of a toothbrush handle (not shown) from the case 11, if the case is desired to enclose only the head of the toothbrush.

A receptacle 21 (FIGS. 1, 2 and 5) for holding antiseptic media 31 is desirably integrally molded from the same material as the case 11 on the major exterior surface 22 of the first portion 13 for ease of manufacture and placement of the antiseptic media 31 in the receptacle 21. It will be appreciated that arrangements other than integral molding of receptacle may be accomplished within the spirit of some embodiments of the present invention. The receptacle 21 has a bottom, or first wall formed by a receptacle-wall portion 23 (FIG. 2 and FIG. 4) of the first portion 13 of the case 11. The receptacle 21 is further defined by at least one wall 25 extending from the exterior surface 22 of the first portion 13 to form the side wall, or walls, as desired, of the receptacle 21. The at least one wall 25 has a top surface 26 being that surface of the receptacle 21 generally farthest from the exterior surface 22.

A plurality of throughholes 27 (FIG. 2 and FIG. 4) are integrally formed during molding, or by later piercing, to be located within the receptacle-wall portion 23 of the first portion 13 and distributed over a preponderance of the receptacle-wall portion 23 of the first portion 13. The throughholes 27 provide a sufficient volume of fluid communication between an inner surface 29 of the case, and more particularly the void formed by the case portions to contain an adjacent toothbrush (not shown), and the interior of the receptacle 21 containing the out-gassing antiseptic media. It is preferred that the receptacle 21 and throughholes 27 are located at that portion of the void intended to receive the wet bristles of the brush. Alternatively, the means for providing fluid communication may include a gas permeable material of the first case portion 13, or at least the receptacle-wall portion 23 thereof. Selection of suitable gas permeable polymers or the like for construction of the case 11, or suitable receptacle portions thereof, are considered to be within the skill of the art.

The antiseptic media 31 is then safely contained within the receptacle 21 by a covering 33 which is tenaciously engaged, such as by ultrasonic welding, heat sealing, adhesives, or the like, to the receptacle, and particularly the top surface 26 of the at least one wall 25, to enclose the antiseptic media 31 within the receptacle 21 in an airtight and tamper-resistant manner. The tenacious engagement of the covering 33 ensures the receptacle contents are resistant to tampering or removal by children.

The antiseptic media 31 is an out-gassing solid containing absorbed antimicrobial agents and is designed to emit antiseptic vapors into the void of the case in order to suppress the growth of bacteria on the head of the toothbrush (not shown).

The antiseptic media 31 is preferably granular in order to present a large surface area and sufficiently granular as to be sized to extend beyond a diameter of the throughholes to keep the grains of the media from entering the void and making direct contact with the toothbrush (not shown).

The composition of the granular, antiseptic media 31 includes an out-gassing, antimicrobial agent selected from thyme oil, thymol, oregano oil, carvacrol, tea tree oil, terpineol, eucalyptus oil, eucalyptol, clove oil, cinnamon oil, eugenol, Peru balsam oil, cinnamic acid, peppermint oil, menthol, geranium oil, geraniol, rosemary oil, verbenone, cedarwood oil, cedrol, pinocarvone, dill oil, anethol, hinokitiol, berberine, ferulic acid, methyl salicylic acid, wintergreen oil, methyl salicylate, bitter orange oil, limonene or a derivative thereof. In accordance with certain embodiments, the out-gassing, antimicrobial agent is thymol, thyme oil, a derivative thereof or a combination thereof. In accordance with other embodiments, the out-gassing, antimicrobial agent is thyme oil. Suitably, the thyme oil includes or contains about 20 to about 50 percent thymol.

The granular, antiseptic media may include a crystalline, out-gassing, antimicrobial agent, inert carrier granules impregnated with an out-gassing, antimicrobial agent, porous beads impregnated with an out-gassing, antimicrobial agent, or a combination thereof.

The inert carrier granules or inert particulate carrier, may include granules of a natural material such as, for example, corn cobs, sawdust, tobacco stalks, coconut shells, bentonite, fullers earth, kaolins, clays, talc, chalk, quartz, attapulgite, montmorillonite, diatomaceous earth, vermiculite, calcite, marble, pumice, sepiolite, dolomite, or a combination thereof. Desirably, the granular, antiseptic media comprises corn solids such as, for example, ground corn cobs, which have been found to be particularly resilient, stable and efficacious for the absorption and release of an out-gassing, antimicrobial agent such as, for example, thymol, thyme oil, a derivative thereof, or a combination thereof, in an environment of repeated wetting and drying. In accordance with certain other embodiments, the granular, antiseptic media may include porous aroma beads impregnated with thymol, thyme oil, a derivative thereof, or a combination thereof. In accordance with certain further embodiments, the inert carrier granules or inert particulate carrier may include a combination of granules of one or more natural material and synthetic materials such as, for example, porous aroma beads.

Advantageously, the granular, antiseptic media also includes a fragrance for remediating an antiseptic odor of the out-gassing, antimicrobial agent. In accordance with certain embodiments, the granular, antiseptic media includes disinfectant granules (i.e., a first inert particulate carrier impregnated with an out-gassing, antimicrobial agent) blended with fragrance granules (i.e., a second inert particulate carrier impregnated with a fragrance) in a select ratio to remediate or mask an antiseptic odor of the out-gassing, antimicrobial agent.

It has been discovered that by blending disinfectant granules with fragrance granules the aromas of the two materials are blended together without reducing the strength and/or efficacy of the out-gassing, antimicrobial agent. Further, blending disinfectant granules with fragrance granules results in a granular, antiseptic media having an improved ability to remediate or mask an antiseptic odor of the disinfectant granules compared to an antiseptic media containing an out-gassing, antimicrobial agent blended directly with a fragrance (i.e., a liquid/liquid blend) in the same ratio.

The fragrance may include an essential oil, a scented or perfume oil, or a combination thereof. As used herein the term "essential oil" refers to a concentrated, hydrophobic liquid which contains volatile aromatic compounds and which has been extracted from a plant-based source material directly through distillation or expression. Suitable essential oils for use as a fragrance in the granular, antiseptic media include, but are not necessarily limited to, anise, benzoin, bergamot, bergamot mint, chamomile, cinnamon, clary sage, clove, elemi, frankincense, ginger, grapefruit, helichrysum, juniper berry, lavender, lemon, lime, linden blossom, neroli, orange including bitter and sweet orange oil, patchouli, peppermint, rosewood, sandalwood, spearmint, tangerine, vanilla, and vetiver. In accordance with certain embodiments, the fragrance may include an essential oil which is also an out-gassing, antimicrobial agent. In accordance with certain other embodiments, the fragrance is cinnamon oil.

As used herein, the terms "scented oil" and "perfume oil" refers to at least one natural or synthetic aroma compound dispersed, diluted or blended in a carrier like propylene glycol, vegetable oil, or mineral oil. In accordance with certain embodiments, the scented oil may include or contain one or more compounds derived from biological sources, such as, for example, aroma compounds derived from animal sources, aroma compounds produced as byproducts of fermentation, absolutes (i.e., fragrant oils extracted primarily from flowers or delicate plant tissues through solvent or supercritical fluid extraction), concretes (i.e., fragrant materials that have been extracted from raw materials such as from plant-based sources, through solvent extraction using volatile hydrocarbons), and alcohol extracts or tinctures of plant-based sources. In accordance with certain other embodiments, the scented oil may contain or include one or more essential oils blended with one or more aroma compounds.

Inert carrier granules or inert particulate carrier materials suitable for preparing the fragrance granules include, but are not limited to, a natural materials or combinations of natural materials selected from corn cobs, sawdust, tobacco stalks, coconut shells, bentonite, fullers earth, kaolins, clays, talc, chalk, quartz, attapulgite, montmorillonite, diatomaceous earth, vermiculite, calcite, marble, pumice, sepiolite, dolomite, porous synthetic materials such as, for example, plastic or polymer aroma beads, and combinations of natural and synthetic materials.

The granular, antiseptic media may be prepared or made by impregnating or infusing a first inert particulate carrier with an out-gassing, antimicrobial agent to produce disinfectant granules, impregnating or infusing a second inert particulate carrier with a fragrance to produce fragrance granules, and blending the disinfectant granules with the fragrance granules in a select or pre-determined ratio to remediate an antiseptic odor of the disinfectant granules. In accordance with certain embodiments, the first and second inert particulate carriers may include the same material. In accordance with certain other embodiments, the first inert particulate carrier may include a first material and the second inert particulate carrier may include a second, different material.

In accordance with certain embodiments, the disinfectant granules may be blended with the fragrance granules in a ratio of about 10:90 to about 90:10. In accordance with certain other embodiments, the disinfectant granules may be blended with the fragrance granules in a ratio of about 50:50. In accordance with certain additional embodiments, additional lots or groups of inert particulate carrier material may be individually treated or impregnated with an out-gassing, antimicrobial agent and/or a fragrance and subsequently blended with the disinfectant granules and the fragrance granules.

As will be understood by those skilled in the art and guided by the teachings herein provided, the exact ratio of disinfectant granules to fragrance granules will depend largely upon out-gassing, antimicrobial agent and fragrance selection.

In accordance with one embodiment, a granular, antiseptic media may be prepared by impregnating a first granular corn cob media with thyme oil containing about 20 to about 50 percent thymol to produce disinfectant granules and impregnating a second granular corn cob media with cinnamon oil to produce fragrance granules. The disinfectant granules may be blended with the fragrance granules to produce a granular, antiseptic media including about 35 to about 60 percent disinfectant granules and about 40 to about 65 percent fragrance granules.

Figure 6:
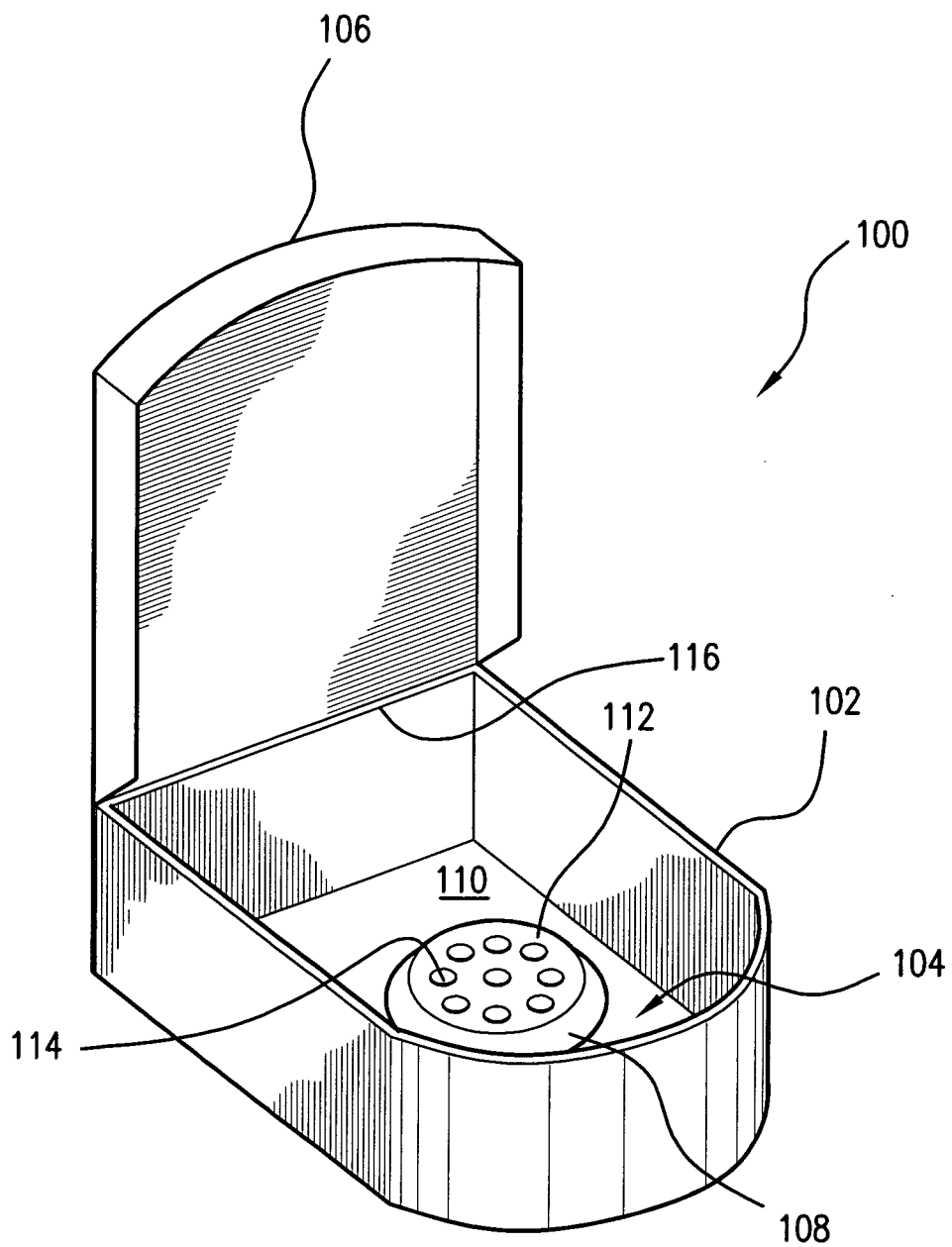
FIG. 6 is an interior perspective view of a mouth guard container in an open position.

Referring to FIG. 6, an exemplary container for sanitizing an article in the form of mouth guard or orthodontic appliance is illustrated. The container 100 includes a case 102 defining a central void 104 and having a lid 106. A receptacle 108 is formed on an interior surface of a bottom wall 110 of the case 102 and extends into the central void 104. The receptacle 108 is sized to accommodate a select quantity of an antiseptic media such as, for example, the granular, antiseptic media 31 described above in conjunction with FIGS. 1-5. The receptacle further includes a covering 112 having a plurality of throughholes 114 for retaining or enclosing the granular, antiseptic media within the receptacle 108 while allowing antiseptic vapors emitted by the granular, antiseptic media to enter the central void 104.

In accordance with certain embodiments, the covering 112 may be tenaciously engaged with the receptacle 108 such as, for example, by ultrasonic welding, heat sealing, adhesives, or the like. In accordance with certain embodiments, the covering 112 may be releasably engaged with the receptacle such that the spent or used granular, antiseptic media may be removed and/or replaced with fresh granular, antiseptic media.

As shown in FIG. 6, the lid 106 may be integrally connected to the case 102 via a living hinge 116. In accordance with certain other embodiments, the lid 106 may be removable or separable from the case 102.

Figure 7:
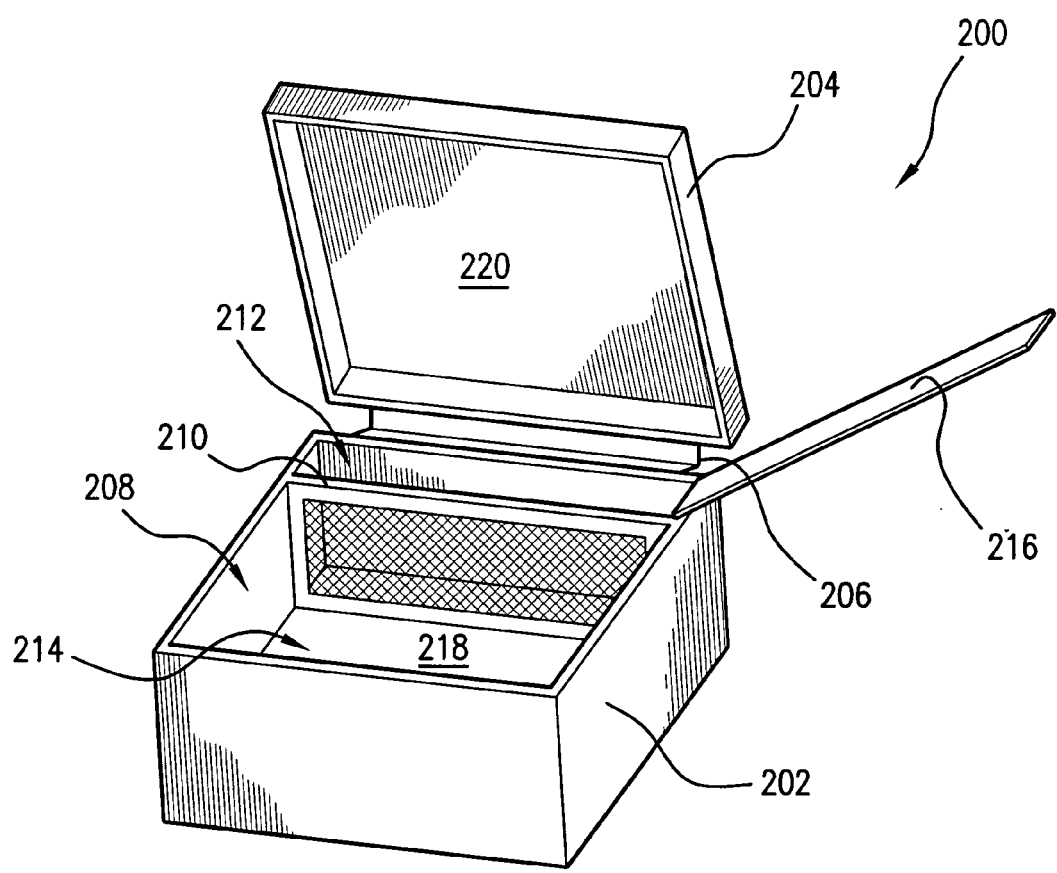
FIG. 7 is an interior perspective view of a container in an open position.

Referring to FIG. 7, another exemplary container for sanitizing an article in the form of sponge, brush or other similar item is illustrated. The container 200 includes a case 202 defining a central void 208 having a lid 204 joined to the case via a living hinge 206. The container includes an interior wall 210 which divides the central void 208 into a receptacle 212 and a cavity 214. The receptacle 212 is dimensioned to contain or enclose a select quantity of a granular, antiseptic media such as, for example, the granular, antiseptic media 31 described above in conjunction with FIGS. 1-5. The cavity 214 is dimensioned to accommodate at least a portion of an article to be sanitized.

The interior wall 210 includes or contains a plurality of throughholes 216 which allows antiseptic vapors emitted from the granular, antiseptic media to enter the cavity 214. The plurality of throughholes 216 may be integrally formed during molding of the case 202, or by later piercing the interior wall 210. Suitably, the throughholes 216 are distributed over a preponderance of the interior wall 210 to provide a sufficient volume of fluid communication between the receptacle 212 and the cavity 214. Alternatively, the interior wall 210 may include or be constructed from a gas permeable material such as, for example, mesh, netting, gas permeable membrane or any other material which readily allows sanitizing or antiseptic vapors produced by the granular, antiseptic media to pass from the receptacle 212 into the cavity 214 of the case 202 while retaining the granular, antiseptic media within the receptacle 212.

The case 202 may further include a cover 216 which closes the receptacle 212 and retains the granular, antiseptic material within the receptacle 212. In accordance with certain embodiments the cover 216 may be tenaciously engaged with the receptacle 212 such as, for example, by ultrasonic welding, heat sealing, adhesives, or the like. In accordance with certain other embodiments, the cover 216 may be in the form of a plug or an integrally formed lid which is releasably engaged with case 202 to allow the removal and/or replacement of used or spent granular, antiseptic media. Suitably, the cover 216 may include perforations or throughholes which allow antiseptic vapors emitted by granular, antiseptic media to enter the interior of the case 202 and, particularly, the cavity 214. In such embodiments, the receptacle 212 thus has two surfaces or walls through which antiseptic vapors may be emitted.

As shown in FIG. 7, the interior wall 210 is positioned parallel to one exterior wall of the case 202 and extends the full width of the case. One skill in the art and guided by the teachings herein provided would understand and appreciate that the interior wall 210 may positioned adjacent any one or more of the side walls and/or may extend parallel to only a portion of a side wall. In accordance with certain further embodiments, the interior wall 210 may be positioned adjacent a bottom wall 218 of the case 202 such that at least a portion of cavity 214 overlays at least a portion of receptacle 212. Alternatively, the interior wall 210 may be positioned adjacent a top wall 220 of the lid 204 such that at least a portion the receptacle 212 overlays at least a portion of the cavity 214 when the container 200 is closed.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A container for sanitizing an article, comprising:
   a case defining a central void sized to accommodate at least a portion of the article;
   a receptacle in fluid communication with the central void; and
   a granular, antiseptic media disposed within the receptacle, the granular, antiseptic media consisting of a blend of individual disinfectant granules and individual fragrance granules in mixed granular form to present a large surface area and with sufficient granularity to remain within the receptacle and not make direct contact with the article, wherein:
   the disinfectant granules are impregnated with an out-gassing, antimicrobial agent selected from the group consisting of thyme oil, thymol, and derivatives thereof and combinations thereof; and
   the fragrance granules are impregnated with a fragrance, wherein the antimicrobial agent and the fragrance are different, the fragrance granules are no impregnated with the antimicrobial agent and the disinfectant granules are not impregnated with the fragrance, and the disinfectant granules are mixed with the fragrance granules in a ratio of about 10:90 to about 90:10.

2. The container of claim 1, wherein the granular, antiseptic media comprises at least one of inert carrier granules impregnated with an out-gassing, antimicrobial agent, or porous beads impregnated with an out-gassing antimicrobial agent.

3. The container of claim 2, wherein the inert carrier granules comprise granules of a natural material selected from the group consisting of corn cobs, sawdust, tobacco stalks, coconut shells, bentonite, fullers earth, kaolins, clays, talc, chalk, quartz, attapulgite, montmorillonite, diatomaceous earth, vermiculite, calcite, marble, pumice, sepiolite, dolomite and combinations thereof.

4. The container of claim 1, wherein the granular, antiseptic media comprises ground corn cobs impregnated with thyme oil, thymol, derivatives thereof, or a combination thereof.

5. The container of claim 1, wherein the granular, antiseptic media comprises porous aroma beads impregnated with thyme oil, thymol, derivatives thereof, or a combination thereof.

6. The container of claim 1, wherein the fragrance granules are blended with the disinfectant granules in a select ratio to remediate an antiseptic odor of the disinfectant granules, the granular, antiseptic media including about 35 to about 60 percent disinfectant granules and about 40 to about 65 percent fragrance granules.

7. A container for sanitizing an article, comprising:
a case defining a central void sized to accommodate at least a portion of the article;
a receptacle in fluid communication with the central void; and
a granular, antiseptic media disposed within the receptacle, the granular, antiseptic media including a granular blend ofL a first inert particulate carrier impregnated with an out-gassing, antimicrobial agent; and a second inert particulate carrier impregnated with a fragrance and not impregnated with the antimicrobial agent, wherein the first inert particulate carrier and the second inert particulate carrier are blended in a select ratio to remediate an odor of the out-gassing, antimicrobial agent.

8. The container of claim 7, wherein the out-gassing, antimicrobial agent is selected from the group consisting of thyme oil, thymol, and derivatives and combinations thereof.

9. The container of claim 7, wherein the out-gassing, antimicrobial agent comprises thyme oil.

10. The container of claim 7, wherein the first inert particulate carrier and the second inert particulate carrier each comprises a granular material selected from the group consisting of corn cobs, porous beads, sawdust, tobacco stalks, coconut shells, bentonite, fullers earth, kaolins, clays, talc, chalk, quartz, attapulgite, montmorillonite, diatomaceous earth, vermiculite, calcite, marble, pumice, sepiolite, dolomite and combinations thereof.

11. The container of claim 7, wherein the fragrance comprises an essential oil, a scented oil or a combination thereof.

12. The container of claim 7, wherein the fragrance comprises cinnamon oil.

13. A method of making the granular, antiseptic media used in the container for sanitizing an article of claim 7 comprising:
impregnating the first inert particulate carrier with the out-gassing, antimicrobial agent to produce disinfectant granules;
impregnating the second inert particulate carrier with the fragrance to produce fragrance granules; and
subsequently blending the disinfectant granules with the fragrance granules in a select ratio to remediate an antiseptic odor of the disinfectant granules.

14. A container for sanitizing an article comprising:
a case defining a central void sized to accommodate at least a portion of the article;
a receptacle in fluid communication with the central void; and
a granular, antiseptic media disposed within the receptacle, the granular, antiseptic media including a granular blend of:
a first granular corn cob media impregnated with only thyme oil, thymol, derivatives thereof or combinations thereof; and
a second granular corn cob media impregnated with a fragrance, wherein the second granular corn cob media is not impregnated with thyme oil, thymol, derivatives thereof or combinations thereof, and the first granular corn cob media and the second granular corn cob media are mixed in a ratio of about 10:90 to about 90:10.

15. The container of claim 14, wherein the fragrance comprises cinnamon oil.

16. The container of claim 14, wherein the first granular corn cob media is blended with the second granular corn cob media in a pre-determined ratio, the pre-determined ratio being about 50:50.

17. The container of claim 14, wherein the article is selected from the group consisting of toothbrushes, hairbrushes, make-up brushes, mouth guards, combs, razors, bottle brushes, scrub brushes, toilet brushes, vegetable brushes, pastry brushes, and basting brushes.

18. The container of claim 10, wherein the first inert particulate carrier and the second inert particulate carrier comprise granular materials having different properties.

19. The container of claim 1, wherein the disinfectant granules are mixed with the fragrance granules in a ratio of about 25:75.

* * * * *